United States Patent
Lynn et al.

(10) Patent No.: US 11,566,225 B2
(45) Date of Patent: Jan. 31, 2023

(54) AUTOMATED SYSTEM FOR PROCESSING A BIOLOGICAL FLUID

(71) Applicant: Fenwal, Inc., Lake Zurich, IL (US)

(72) Inventors: Daniel Lynn, Spring Grove, IL (US); Katherine Radwanski, Des Plaines, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 14/505,816

(22) Filed: Oct. 3, 2014

(65) Prior Publication Data

US 2016/0097034 A1    Apr. 7, 2016

(51) Int. Cl.
*C12N 5/078*    (2010.01)
*A61M 1/02*    (2006.01)

(52) U.S. Cl.
CPC ......... *C12N 5/0641* (2013.01); *A61M 1/0209* (2013.01); *A61M 1/0272* (2013.01); *A61M 2202/0429* (2013.01)

(58) Field of Classification Search
CPC .. B01L 3/502; B01L 3/5027; B01L 3/502715; B01L 3/502738; B01L 3/52; C12N 5/0634; C12N 5/0641; C12N 5/0461; A61M 1/0209; A61M 1/0272; A61M 2202/0429
See application file for complete search history.

(56) References Cited

U.S. PATENT DOCUMENTS

| | | | |
|---|---|---|---|
| 5,836,934 A * | 11/1998 | Beshel | A61M 1/0218 210/231 |
| 5,906,915 A | 5/1999 | Payrat et al. | |
| 6,132,413 A | 10/2000 | Mathias et al. | |
| 2003/0106861 A1* | 6/2003 | Gibbs | A61M 1/3633 210/806 |
| 2007/0020607 A1* | 1/2007 | Meryman | A01N 1/02 435/2 |
| 2007/0048194 A1* | 3/2007 | Schulein | B01L 3/502715 422/400 |
| 2009/0239208 A1 | 9/2009 | Mayaudon et al. | |
| 2009/0325220 A1* | 12/2009 | Reed | G01N 21/6428 435/31 |
| 2011/0117647 A1 | 5/2011 | Mayaudon et al. | |
| 2012/0225419 A1* | 9/2012 | Min | A61M 1/0209 435/2 |

FOREIGN PATENT DOCUMENTS

| | | |
|---|---|---|
| EP | 2777727 A1 | 9/2014 |
| EP | 2777754 A1 | 9/2014 |
| WO | WO 2004/058046 A2 | 7/2004 |
| WO | WO 2005/065739 A1 | 7/2005 |
| WO | WO 2012/139017 A1 | 10/2012 |

OTHER PUBLICATIONS

Extended European Search Report for EP Application No. 15188321.2-1651 dated Feb. 9, 2016.

* cited by examiner

*Primary Examiner* — Renee Claytor
*Assistant Examiner* — Susan E. Fernandez
(74) *Attorney, Agent, or Firm* — Cook Alex Ltd (57) ABSTRACT

Systems and methods for processing biological fluids are disclosed. The systems and methods use a reusable hardware unit and a disposable fluid processing circuit that mounts onto the reusable hardware unit. The system and method, under the direction of a pre-programmed controller allow for automatically, opening one or more flow paths to effect addition of one or both parts of an additive solution to a biological fluid component.

11 Claims, 4 Drawing Sheets

AUTOMATED SYSTEM FOR PROCESSING A BIOLOGICAL FLUID

FIELD OF THE DISCLOSURE

The present disclosure is directed to systems and methods for the automated processing of a biological fluid. More particularly, the present disclosure is directed to automated systems and methods for processing red blood cells including, without limitation, the automated combining of a multi-part additive solution and addition of the additive solution to separated red blood cells.

BACKGROUND

In the field of biological fluid processing, such as but not limited to blood processing, it is quite common to separate the biological fluid into two or more components. In blood processing, in particular, whole blood is commonly separated into red blood cells, plasma and/or platelets. Red blood cells that have been separated from whole blood and collected are later transfused to a patient in need of red blood cells. For example, red blood cells (hereinafter "RBCs") may be administered to a patient suffering from a loss of blood due to trauma, as a post-chemotherapy treatment, or as part of a treatment of one or more blood borne diseases, such as certain anemias and the like. If not administered soon after collection from a donor, RBCs may be stored for some period of time prior to transfusion. The storage period may be anywhere from a few days to several weeks.

Prolonged storage of RBCs can (negatively) affect RBC function. In order for the RBCs to be suitable for transfusion to a recipient, RBCs must maintain adequate cell function and metabolism. For example, RBCs must maintain an adequate concentration of adenosine triphosphate (ATP) and 2,3-DPG. In addition, the presence of lactate must not be too high in the stored RBCs. Still further, stored RBCs must have acceptably low levels of hemolysis. Typically, an acceptable level of hemolysis is below 1.0% (in, for example, the U.S.) and 0.8% (in Europe) after 42 day storage.

Media for providing a storage environment for RBCs that will allow cell function and cell metabolism to be preserved and maintained have been developed and are commonly used. The media developed for RBCs can prolong the storage life of RBCs for up to 42 days. Such media (or "additive solutions") often include a nutrient for the RBCs, a buffer to help maintain the pH of the RBCs, electrolytes, a RBC membrane-protecting compound and other additives to enhance and extend the life of the RBCs.

Additive solutions are often provided in plastic containers whereby the containers and their contents must be sterilized prior to their use. Autoclaving or steam sterilization is commonly used in the sterilization of medical products, medical or biological solutions, the plastic containers that contain the solutions, and the disposable fluid processing circuits which include the processing containers, the fluids and the plastic tubing that allows for flow through the fluid processing circuit.

While autoclaving is an effective and efficient way to sterilize the products and kits used in blood processing, it is not a suitable method for certain additive solutions. As discussed in U.S. Pat. No. 5,906,915, additive solutions that contain sugar undergo carmelization when exposed to the high temperatures of autoclaving at other than an acidic pH. Examples of such additive solutions that may be susceptible to carmelization are disclosed in U.S. Patent Application Publication No. 2009/0239208 and 2011/0117647, the contents of which are incorporated by reference herein. The additive solutions disclosed therein are, hypotonic, synthetic aqueous storage solutions for the prolonged storage of RBCs and include adenine, mannitol, sodium citrate, sodium phosphate, and glucose (dextrose) as the nutrient. Such solutions are provided in two separate parts (in, for example, two separate containers), each part having a different pH and being separately sterilized. The two parts are combined prior to or at the time of use. The two parts of the additive solution are typically combined in a manual process whereby the user or operator establishes an open flow path between the separate containers holding the two parts of the additive solution and/or the container of the RBCs. Typically, the user or operator bends and breaks internal frangible connectors or cannulas that block flow between containers. The use of frangible connectors is well known and frangible connectors are described in U.S. Pat. No. 6,132,413, the contents of which are incorporated by reference herein.

While the additive solutions of the type described herein are very effective in maintaining and prolonging the storage life of RBCs, the need to manually combine the two parts of the additive solution and then manually combine the additive solution with the collected RBCs can make the process of blood component processing more cumbersome and more time consuming. Manual processes may also introduce operator-to-operator variability.

Thus, it would be desirable to provide a system and method wherein at least the steps of combining the parts of a two-part additive solution and/or combining the additive solution with the collected RBCs or other blood component are automatically performed in a device, under the direction of a pre-programmed controller. It may also be desirable to provide a system and method whereby the combination, mixing and/or addition of the additive solution can automatically commence at a selected time, under the direction of a pre-programmed controller. It may also be desirable to pre-program the controller to direct the combination, mixing and addition of the additive solution in several different ways depending, at least in part, on the configuration of the disposable fluid processing circuit. It may also be desirable to provide disposable fluid processing circuits with different mixing chambers that may provide for different combining, mixing and adding sequences. It may also be desirable to control the amount of additive solution added to the blood component (i.e., making the additive solution volume proportional to the volume of the collected blood component, such as packed red blood cells for optional blood storage and blood product standardization.) Finally, it may also be desirable to standardize the addition of two-part additive solutions to a blood component and substantially eliminate operator-to-operator variability.

SUMMARY

In one aspect, the present disclosure is directed to a system for processing a biological fluid. The system includes a reusable hardware unit and a disposable fluid processing circuit. The reusable hardware unit includes two or more container-holders, a flow path opening device associated with at least one of said two more container holders, and a pre-programmed controller for actuating the flow path opening device at a selected time. The disposable fluid processing circuit includes at least three containers wherein one of the containers contains a first part of an additive solution and another of said containers contains a second part of an additive solution. The disposable fluid processing circuit includes at least one openable flow path joining the at least three containers. The openable flow path includes a flow blocker.

In another aspect, the present disclosure is directed to a method for combining a biological fluid with two parts of a biological fluid additive solution. The method includes mounting selected containers of a disposable fluid processing circuit of the type described above, wherein the selected containers include at least a container of a component of a biological fluid and a container of one part of an additive solution, onto the reusable hardware unit of the type also described above. The method includes automatically opening a flow path between the container containing the blood component and at least the container containing one part of an additive solution. The method further includes adding a second part of an additive solution from a separate container to the container containing a component of a biological fluid.

DETAILED DESCRIPTION OF THE EMBODIMENTS

Figure 1:
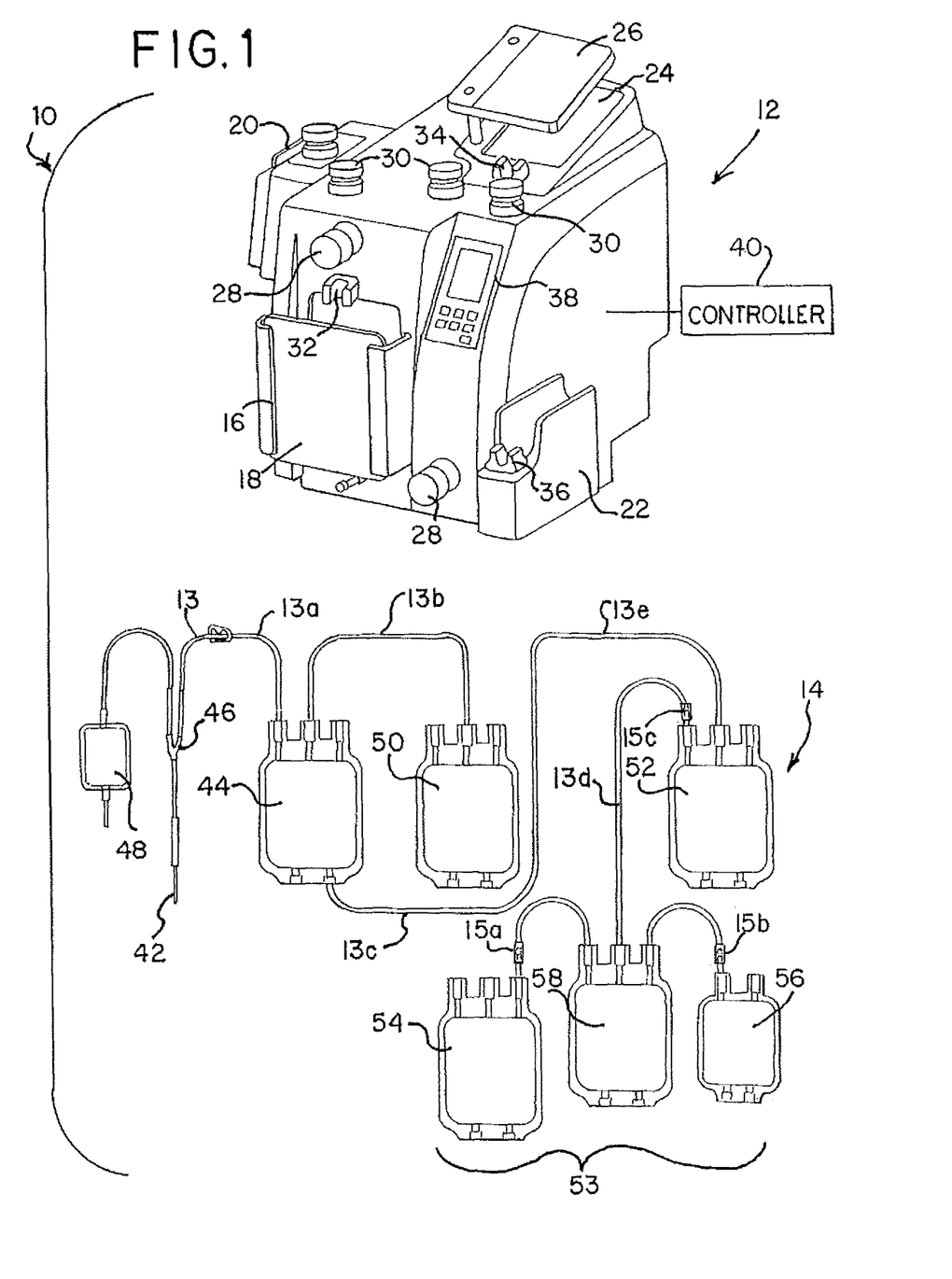
FIG. 1 is a schematic view of a system including the reusable hardware unit and the disposable component in accordance with the present disclosure.

Turning now to the Figures, FIG. 1 shows system 10 in accordance with the present disclosure. System 10 includes a reusable hardware unit 12 and a disposable fluid processing circuit which includes a plurality of flexible, plastic containers in openable flow communication through tubing 13 defining a flow path (which may be made up of tubing segments 13a-13e). In use, at least a portion of disposable fluid processing circuit 14 is mounted on reusable hardware unit 12. Through the action of one or more presses under the direction of a pre-programmed controller, biological fluid and the separate components thereof may be expressed and transferred as desired within the disposable fluid processing circuit 14.

As shown in FIG. 1, reusable hardware unit 12 may include one or more container compartment areas. For example, reusable hardware unit 12 may include a container compartment area 16 for receiving a flexible plastic container of biological fluid such as, for example, whole blood, which is to be separated into two or more components or a blood component that has already been separated from whole blood such as, but not limited to, packed red blood cells. Container holding area 16 defines a space between the face of reusable hardware unit 12 and a moveable, press plate 18. Press plate 18 may be moveable under the direction of the controller by either mechanical or pneumatic means.

When activated, press plate 18 presses on the outer surface of a (primary) container, which in turn expresses fluid to one or more of the pre-attached satellite containers as will be described in greater detail below. Container compartment 16 may also be associated with a scale or other means for sensing or determining the weight or volume of the fluid inside container 16.

Reusable hardware unit 12 may include other container holding compartments, such as compartment 20, also for receiving another container of disposable fluid processing circuit 14. In one embodiment, compartment 20 may hold a satellite container for receiving one of the separated components from the primary container held within compartment 16. Compartment 16 may be a slot, other cavity, or chamber where a satellite container may be placed. Additional compartments may include compartment 22, also for receiving a container of the disposable fluid processing circuit 14. A further container compartment 24 may also be provided, as shown in FIG. 1. As with compartment 16, container compartment 24 may be provided with a press plate 26, which may also effect expression of fluid from the container housed within compartment 24. Compartment 24 may also be adapted to receive a blood cell filter, such as a leukoreduction filter which may be subjected to the pressing action of press plate 26 to advance the filtration process. Compartment 24 may also be associated with a scale or other detector for measuring the volume or weight of fluid within the container held within compartment 24 and/or allow for the metering of a selected volume of the solution from the container placed within compartment 24.

Reusable hardware unit 12 may further include one or more sensors 30 for detecting flow conditions through tubing segments 13 of disposable fluid processing circuit 14. Sensors 30 may have only a sensing function or may include other functions such as a flow control. Other components of reusable hardware unit 12 include sealers 28 which provide a sealing capability for sealing a tube segment 13 so as to restrict flow from one container to another, as necessary, and/or isolate a portion of disposable fluid processing circuit 14 from another portion.

As further shown in FIG. 1, reusable hardware unit includes one or more flow path opening devices 32, 34 and 36 associated with or in proximity to the container holding compartments described above. Flow path opening devices 32, 34 and 36 act on flow blockers (such as frangible connectors or cannulas) contained within the flow paths, i.e., tubing 13 of the disposable fluid processing circuit 14. Flow path opening devices, under the direction of a controller, provide for mechanical breakage of the flow blockers or frangibles in the disposable processing set to open flow paths between different parts of disposable fluid processing circuit 14, as required. Automated flow path opening devices are described in greater detail in U.S. Patent Application Publication No. US2014/0263529, which is incorporated by reference herein in its entirety.

As further seen in FIG. 1, reusable hardware unit 12 includes a display/control panel 38. Display/control panel 38 displays status information of the processing procedure, as well as provides an interface with the operator. Display/control pad 38 communicates with a pre-programmed controller that is housed within reusable hardware unit 12 and includes pre-programmed instructions for the opening of flow paths, action of the press plates, etc., in response to conditions sensed by the optical sensors, weight scales and other detectors which communicate with controller 40 and/or to other conditions during the biological fluid processing described in greater detail below.

As shown in the lower half of FIG. 1, system 10 also includes a disposable fluid processing circuit 14 adapted for mounting onto reusable hardware unit 12. Disposable fluid processing circuit 14 includes a plurality of containers for the collection, processing, transfer, and storage of the biological fluid and its components. The disposable fluid processing circuit 14 shown in FIG. 1 and described below is representative of a disposable fluid processing circuit 14 that may be used in accordance with the systems and methods of the present disclosure. Disposable fluid processing circuits 14 with fewer or more containers may also be used in accordance with the present disclosure and the specific configuration of the disposable fluid processing circuit 14 shown in FIG. 1 is provided for illustrative purposes only and not for limitation.

In one embodiment, disposable fluid processing circuit 14 may include a primary container 44 for receiving and holding the biological fluid to be processed. In one embodiment, the fluid may be whole blood collected from a donor. In that regard, disposable fluid processing circuit 14 may further include a donor access device 42, such as a needle or a thin cannula for withdrawing whole blood from a donor. As shown in FIG. 1, disposable fluid processing circuit 14 may further include a branched connector 46 in flow communication with access device 42. One of the flow paths extending from branched connector 46 communicates with primary container 44, while the other flow path branching from branch connector 46 may optionally communicate with a sample pouch 48 for obtaining a pre-donation sample of whole blood.

In accordance with typical blood collection methods, whole blood collected in primary container 44 may be subjected to a separation procedure to separate the whole blood into its constituent components. In one embodiment, container 44 may be subjected to a centrifugal field to separate the whole blood into more dense and less dense layers. Whole blood, once subjected to a centrifugal field, will separate with the more dense red blood cells settling to the bottom of a container, and a supernatant layer of plasma and possibly platelets forming a top layer in the container. Depending on the centrifugation conditions, a middle "buffy coat" layer may also be present. Once separated, these components may be expressed into one or more satellite containers of disposable fluid processing circuit 14. For example, disposable fluid processing circuit 14 may include a satellite container 50 which may be used to receive the expressed top plasma layer and a satellite container 52 which may be used to receive the separated red blood cells from primary container 44.

As shown in FIG. 1, disposable fluid processing circuit 14 may also include an additive solution sub-assembly 53 of containers of additive solution and optional mixing containers. For purposes of illustration only, disposable fluid processing circuit 14 and, more particularly, pre-attached additive solution sub-assembly 53 may include a container 54 for holding a first part of an additive solution and a container 56 for holding a second part of the additive solution. An optional mixing container 58 may also be provided, in which both parts of the additive solution may be mixed. Regardless of whether a mixing container is utilized, additive containers 54 and 56 including additive solutions Part I and Part II are preferably in pre-attached, openable liquid flow communication with container 52 in which separated red blood cells are held. For example, Part I of the additive solution may include the higher pH component of the solution. In one embodiment, Part I may include sodium citrate, sodium phosphate, adenine and mannitol. Part II may include dextrose (glucose). Further details of the additive solution sub-assembly as well as alternative configurations of the additive solution containers 54 and 56 relative to the container for holding red blood cells (RBCs) will be described in greater detail below. In a preferred embodiment, however, the additive solution sub-assembly 53 is pre-attached to disposable fluid processing circuit 14 and, in fact, is part of disposable fluid processing circuit 14 to provide a closed or functionally closed processing system.

Although a detailed discussion of the entire whole blood collection and separation process using reusable hardware unit 12 is beyond the scope of the present disclosure, a brief and general discussion of the initial separation process is set forth below. After centrifugation (or other separation process), primary container 44 of disposable fluid processing circuit 14 having the biological fluid or whole blood separated into layers may be inserted into container holding compartment 16. Typically, tubing segment 13b adjacent to the outlet port of container 44 is threaded through flow path opening device 32, sealer 28 and optical sensor 30 proximate to compartment 16 of reusable hardware unit 12. Satellite containers 50 and 52 may be placed in the container holding compartments 20 and 22. Tubing segment 13e may be threaded through flow opening device 36 and sealer 28 proximate to compartment 22. With the containers in place, the system (pre-programmed to actuate plate 18 and compress container 44 to express the layers of blood) causes red blood cells and plasma to flow to their respective containers. The container is compressed until cells are detected in the flow path of tubing segment 13b by optical sensor 30, after which the flow paths to containers 50 and 52 are closed by sealers 28, respectively.

In one embodiment, the part of disposable fluid processing circuit 14 that includes the containers 44 and 50 (used in the initial separation of blood into its components) may be removed from reusable hardware units 12, and containers of the additive solution sub-assembly 53 are mounted on the reusable hardware unit 12. Red blood cell container 52 may remain mounted or otherwise associated with reusable hardware unit 12. In addition, if desired, the used portion of disposable fluid processing circuit 14 may be severed from the RBC container with the plasma container 50 subjected to further processing, if desired, while the remaining used containers and tubing are discarded. In an alternative embodiment, reusable hardware unit 12 may be modified to include additional container holding compartments, press plates, sensors, ceiling elements, and flow opening devices, i.e., frangible breakers, such that the entire or substantially most of the disposable fluid processing circuit 14 may be mounted on the reusable hardware unit 12, without the need for removing a portion of the circuit and replacing it with another portion of the circuit. In any event, once container 52 has received the red blood cells from primary container 44, the red blood cells may be further processed in/or combined with additive solution in accordance with the present disclosure, as will now be described.

Figure 2:
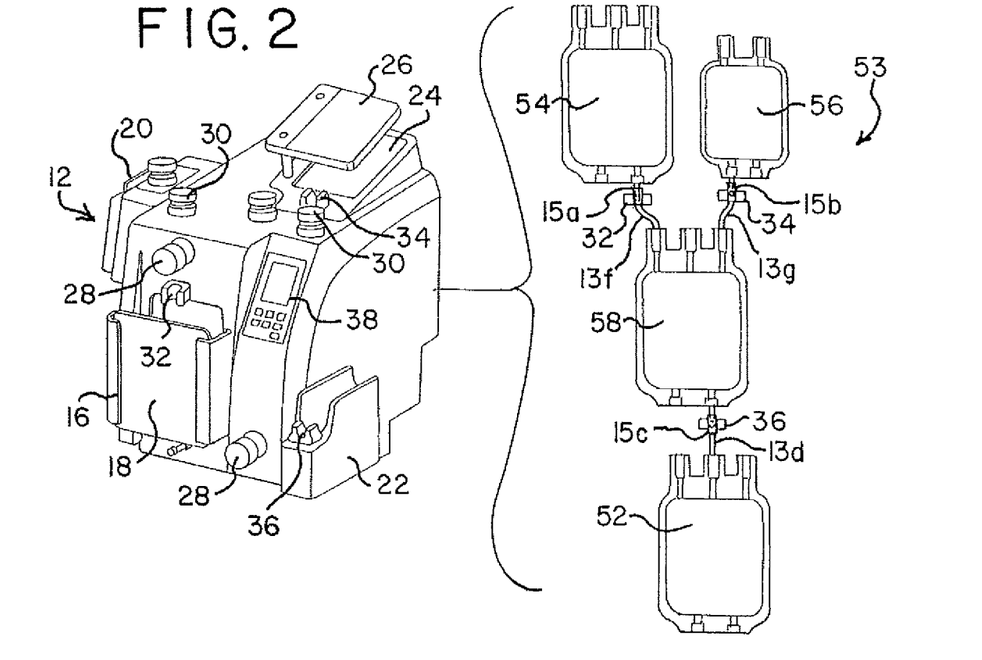
FIG. 2 is a schematic view of the system including the reusable hardware portion and a portion of one embodiment of the disposable processing set.

With reference to FIG. 2, there is shown an additive solution sub-assembly 53 with a red blood cell container 52. Additive solution sub-assembly 53 may include at least containers 54, 56 and 58. As indicated above, container 54 may hold Part I of an additive solution, while container 56 may hold Part II of a two-part additive solution, although the designation of containers 54 and 56 to specific parts of a two-part additive solution is not critical. Each of the containers 54 and 56 is in openable flow communication with a mixing container 58. Mixing container 58, as shown in FIGS. 1 and 2, is pre-attached to the RBC container 52.

Tubing segments 13f and 13g define flow paths from containers 54 and 56, respectively, and each are in openable liquid flow communication with mixing container 58. As shown in FIG. 2, tubing segments 13f and 13g and or containers 54 and 56 include flow blockers, such as frangible cannulas 15a and 15b. As shown schematically in FIG. 2, flow blockers 15a and 15b are placed within flow opening devices; i.e., frangible cannula breakers 32 and/or 34 of reusable hardware unit 12. It is not critical which flow blocker is associated with which flow opening device of reusable hardware unit 12. In addition, flow path 13d between mixing container 58 and RBC container 52 may include flow blocker 15c, and may also be inserted into and acted upon by a flow-opening device (e.g., 36) of reusable hardware unit 12.

System 10 may be pre-programmed to open flow paths 13f and 13g at a selected point of time. In one embodiment, where the entire circuit (kit) 14 is mounted onto reusable hardware unit 12 at the beginning of a procedure, flow paths within tubing segments 13f and 13g may be opened at any time prior to opening of flow path in tubing segment 13d (e.g., in parallel with the initial separation of the biological fluid or whole blood). Flow path in tubing segment 13d may then be programmed to open any time after the initial separation into, for example, plasma and packed RBCs, is complete. In another embodiment, if subassembly 53 is loaded separately (after initial separation) the flow path within tubing segments 13f, 13g and 13d may be opened at any time after the subassembly has been mounted on reusable hardware unit 12. System 10 and, more particularly, controller 40 may be pre-programmed to open flow paths 13f and 13g simultaneously or sequentially to deliver the contents of each container (Parts I and II of additive solution) to mixing container 58. Containers 54 and 56 may be inserted into, for example, container holding compartments 16 and 24 of reusable hardware unit 12 where press plates 18 and 26 may be activated to compress containers 54 and 56 and express liquid from each container to mixing container 58. Once introduced into mixing container 58, the system (based on the pre-programmed instructions of the controller), may cause flow path opening device 36 or other flow opening devices of reusable hardware units 12 to open flow path 13d and deliver the combined additive solution to red blood cell container 52.

Figure 3:
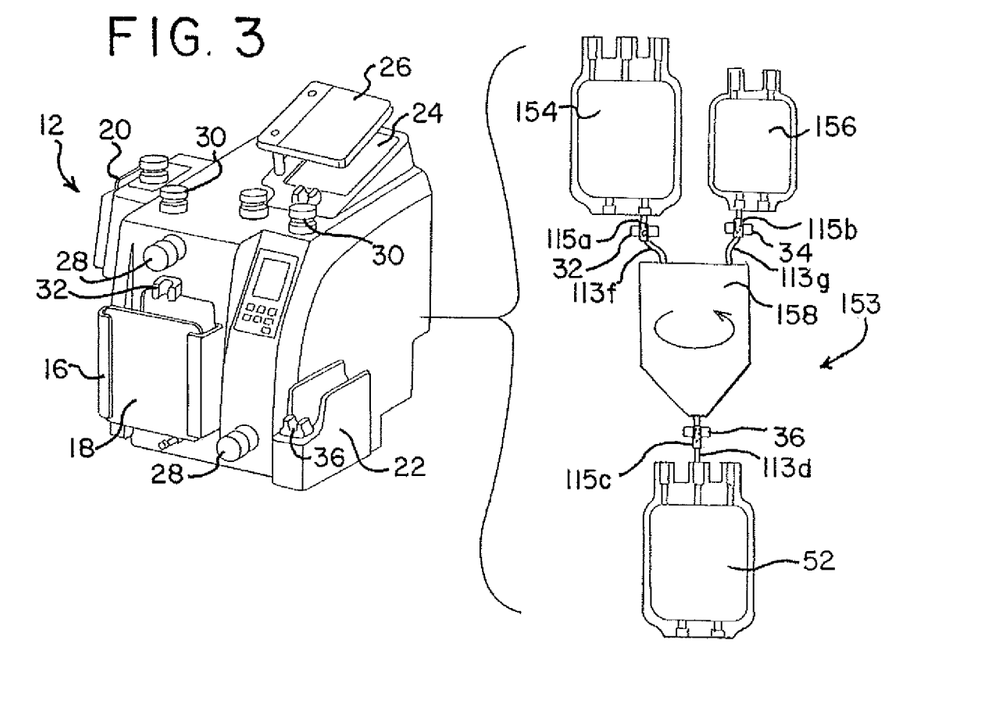
FIG. 3 is a schematic view of the system including the reusable hardware portion and a portion of a second embodiment of the disposable processing set.

FIG. 3 shows a further embodiment 153 of the additive solution sub-assembly 53 described above in connection with FIG. 2. In most material respects, the additive solution sub-assembly 153 of FIG. 3 resembles the additive solution sub-assembly in FIG. 2. In the embodiment of FIG. 3, however, mixing container 158 may be provided with an internal configuration to promote the mixing of additive solutions Part I and Part II. In one embodiment, mixing container 158 may have an internal restricted flow path to create a Venturi effect within the chamber of container 158. This promotes the mixing of solution Parts I and Part II prior to delivery of the combined additive solution to RBC container 52. In all other respects, the method of mounting the additive solution sub-assembly 153 is substantially as described above in connection with FIG. 2, with tubing segments 113f-113g corresponding to the tubing segments 13f-13g described in FIG. 2, and flow blocking members, i.e., frangible cannulas 115a-115c corresponding to 15a-15c of FIG. 2, respectively.

Figure 4:
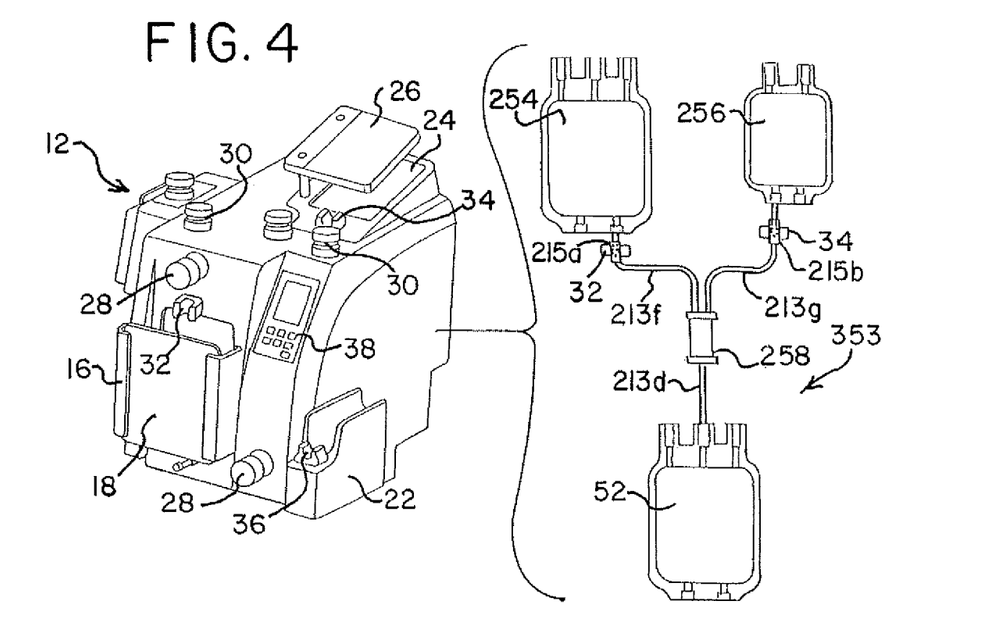
FIG. 4 is a schematic view of the system including the reusable hardware portion and a portion of a third embodiment of the disposable processing set.

In a further alternative shown in FIG. 4, mixing container 258 may be provided in the form of a smaller sized bubble trap or other similar device that affects the mixing of the additive solutions Part I and Part II contained in containers 254 and 256, respectively. In all other respects, the method of mixing and adding the additive solution of container 52 is substantially the same, as previously described. As shown in FIG. 4, flow blockers 215a-215b may be placed within flow opening devices 32 and 34 of the reusable hardware unit 12. Under the direction of the controller, the frangible cannulas or flow blockers may be broken, as described, for example, in U.S. Patent Application Publication No. US2014/0263529, which has been previously incorporated by reference.

Figure 5:
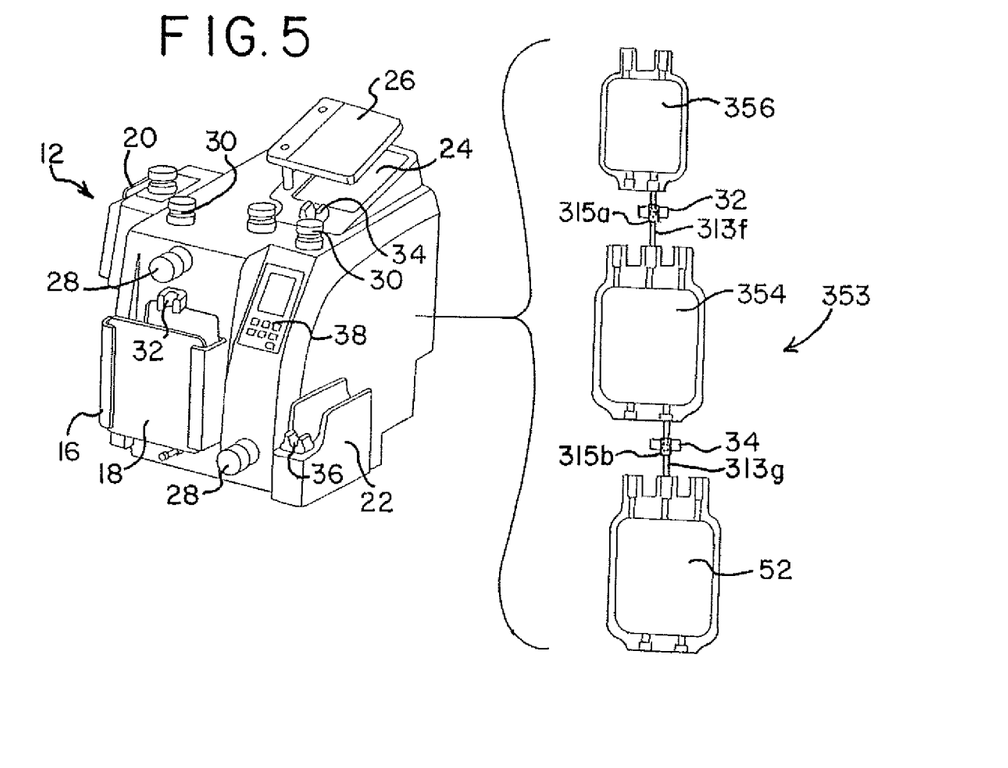
FIG. 5 is a schematic view of the system including the reusable hardware portion and a portion of a fourth embodiment of the disposable processing set.

FIG. 5 shows a further embodiment of an additive solution sub-assembly that utilizes the sequential addition of Part I and Part II of the additive solution components to the red blood cells in RBC container 52. In this embodiment of FIG. 5, the containers 356 and 354 are placed in sequence rather than in parallel, relative to the red blood cell container 52. Tubing segments 313f and 313g that include flow blockers 315a and 315b are inserted onto the reusable hardware unit 12 within any two of the flow opening devices 32, 34 or 36. Under the direction of the controller 40, one of the flow opening devices, for example 32, is actuated and establishes open flow communication between container 356, which contains, for example, Part II of the additive solution and container 354, which contains Part I of the additive solution. Thus, additive solution Part II is first added to additive solution Part I and once combined, the solution is then introduced into red blood cell container 52 by activating flow opening device (e.g., 34) under the direction of the controller 40 at a selected time.

Figure 6:
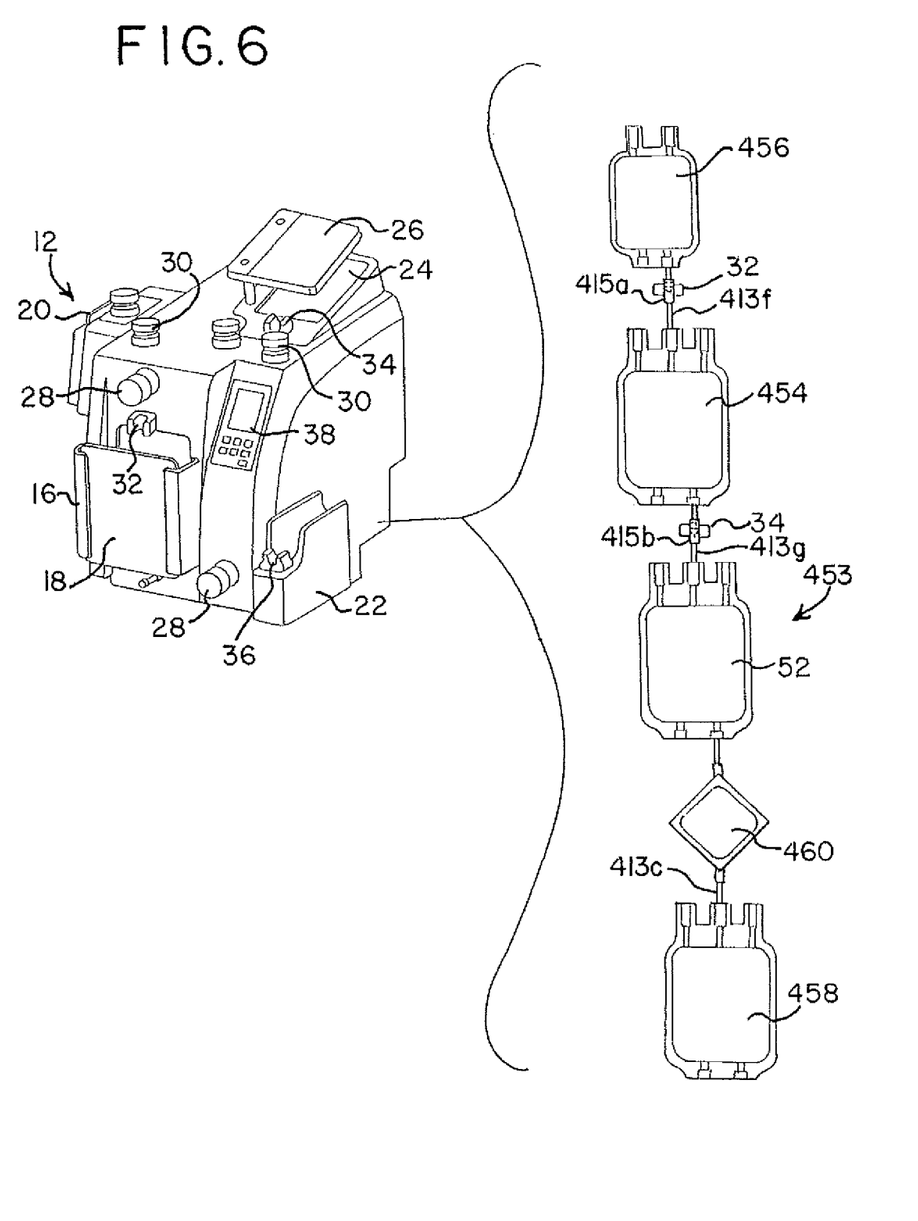
FIG. 6 is a schematic view of the system including the reusable hardware portion and a portion of a fifth embodiment of the disposable processing set.

In a further embodiment shown in FIG. 6, the additive solution sub-assembly 453 includes the sequential arrangement of containers 456 and 454, relative to red blood cell container 52, as previously described. In addition, the embodiment of FIG. 6 may also be provided with a blood cell, i.e., leukoreduction filter 460, downstream of the red blood cell container 52 and a final red blood cell filtrate container 458, as shown in FIG. 6. In accordance with the embodiment of FIG. 6, flow blocker 415b, which is placed within flow opening device 34 of reusable hardware unit 12 may be opened first, allowing additive solution Part I to flow from container 454 into red blood cell container 52. At that point, the combined solution of red blood cells or suspension of red blood cells with Part I of the additive solution may be filtered through leukoreduction filter 460 and collected in red blood cell filtrate container 458. The system may then prompt flow opening devices 32 to open flow blockers 415a and establish an open flow path between container 456 (which includes Part II of the additive solution) and the remaining containers in the sub-assembly 453. The solution, i.e., Part II of the additive solution, in container 456 flows through containers 454, 52 and 460, acting as a rinse that rinses the remainder of the system and, in particular, filter 460. The Part II solution of additive solution is then likewise collected in filtrate container 458.

In accordance with methods and systems described herein, the operator's involvement may be limited to (a) mounting fluid circuit 14 either at the beginning of a procedure or loading subassembly 53 after the initial separation, (b) selecting the procedure type and circuit 14 (via the user interface, i.e., display/control panel 38), and (c) breakdown (removal) of circuit 14 after the procedure. In accordance with one embodiment of the present disclosure, initial separation of the biological fluid, (e.g., whole blood) may be achieved by the controller causing plate 18 to compress container 44 and express plasma into container 50 and RBCs into container 52. Once an optical sensor 30 detects the presence of RBCs in the flow path of a tube expressing plasma, controller 40 causes the activation of plate 18 to stop. In one embodiment, at this point the system (under the direction of the controller 40) may cause Parts I and II of the additive solution to be combined and then added to the packed RBCs (container 52).

Alternatively, Parts I and II can be combined during initial separation and then added to the packed RBCs once the initial separation is completed/stopped, as described above. In a further alternative embodiment, the weight of packed RBCs may be determined by weight scales integrated with container holders. Once a selected weight of packed RBC's is detected, the system calculates the appropriate volume of each of the Parts I and II solutions (based on the weight) to be added to container 52 and (under the direction of controller 40) activates compression plates, to deliver the desired volumes for optimal storage conditions.

Other Aspects

In addition to the aspects set forth above, there are other aspects of the present subject matter which may be embodied separately or together in the devices and systems described and claimed below. These additional aspects may be employed alone or in combination with other aspects of the subject matter described herein and the description of these aspects together is not intended to preclude the use of these aspects separately or the claiming of such aspects separately, or in different combinations as set forth in the claims appended hereto.

In a first aspect, a system for processing biological fluid is provided. The system includes a reusable hardware unit that itself includes two or more container holders, a flow path opening device associated with at least one of the two or more container holders and a controller for actuating the flow path opening device at a selected time. The system also includes a disposable fluid processing circuit with at least three containers wherein one of the containers holds a first part of an additive solution and another of the containers contains a second part of an additive solution. The disposable fluid processing circuit includes an openable flow path joining at least the three containers and a flow blocker in the openable flow path.

A second aspect of the present subject matter includes the system in accordance with the first aspect described above wherein the reusable hardware unit includes at least one sensor for determining the selected time.

A third aspect of the present subject matter includes the system in accordance with the second aspect wherein the sensor communicates with a controller.

A fourth aspect of the present subject matter includes the system of any one of the second or third aspects described above, wherein the sensor senses the amount of a blood component within a container of the disposable fluid processing circuit.

A fifth aspect of the present subject matter includes the system of the fourth aspect wherein the amount of the blood component includes the weight of the blood component within the container.

A sixth aspect of the present subject matter includes the system in accordance with any of the first through fifth aspects wherein the controller is programmed to actuate the flow opening device at a selected time.

A seventh aspect of the present subject matter includes the system of any one of the first through sixth aspects further including a first flow path opening device and a second flow path opening device wherein the controller is programmed to actuate the first flow opening device and second flow path opening device at the selected time.

An eighth aspect of the present subject matter includes the system of any one of the preceding first through seventh aspects wherein one of the containers of the disposable fluid processing circuit includes a mixing chamber in openable flow communication with at least the containers that contain one of the parts of the additive solution.

A ninth aspect of the present subject matter includes the system in accordance with the eighth aspect wherein the mixing chamber includes a flow path restriction for mixing parts of the additive solution.

A tenth aspect of the present subject matter includes the system in accordance with any one of the first through ninth aspects wherein the disposable fluid processing circuit includes a filter for removing a selected blood component from the biological fluid.

An eleventh aspect of the present subject matter includes the system in accordance with any one of the first through tenth aspects wherein the disposable fluid processing circuit includes a first container containing a first part of an additive solution, a second container containing a second part of the additive solution, a third container in openable direct flow communication with at least one of the first and second containers, a fourth container and a fifth container in flow communication with the fourth container.

A twelfth aspect of the present subject matter includes the system in accordance with any one of the first through eleventh aspects wherein the second part of the additive solution includes a sugar.

A thirteenth aspect of the present subject matter includes the system in accordance with any one of the first through twelfth aspects wherein the first part of the additive solution includes sodium citrate, sodium phosphate, mannitol, and adenine.

In the fourteenth aspect of the present subject matter, a method for combining biological fluid with two parts of biological fluid additive solution is provided. The method includes mounting selected containers of a disposable fluid processing circuit made in accordance with any one of the first through thirteenth aspects wherein the selected containers include at least a container of a component of a biological fluid and a container of one part of the additive solution on a reusable hardware unit in accordance with any one of the first through thirteenth aspects. The method further includes automatically opening a flow path between the container of a blood component and at least one container of a one-part additive solution. The method further includes adding a second part of the additive solution from a container to the container of a component of a biological fluid.

A fifteenth aspect of the present subject matter includes the method in accordance with the fourteenth aspect including the step of automatically opening a flow path between the container of the blood component and the container of the second part of the additive solution.

A sixteenth aspect of the present subject matter includes the method in accordance with the fifteenth aspect including the steps of combining the first part of the additive solution with the second part of the additive solution and adding the combined additive solution to the container of the biological fluid component.

A seventeenth aspect of the present subject matter includes the method in accordance with the sixteenth aspect including the step of mixing the first part of the additive solution with the second part of the additive solution prior to adding the combined additive solution to the container of the biological fluid component.

An eighteenth aspect of the present subject matter includes the method of any one of the fourteenth through sixteenth aspects including the step of separately adding the first part of the additive solution and the second part of the additive solution to the biological fluid component simultaneously.

A nineteenth aspect of the present subject matter includes the method of any one of the fourteenth through seventeenth aspects further comprising the step of passing the biological fluid component combined with at least one of the first and second parts of the additive solution through a filter.

A twentieth aspect of the present subject matter includes the method in accordance with the nineteenth aspect including the step of rinsing the filter with one of the first and second parts of the additive solution.

A twenty-first aspect of the present subject matter includes the method in accordance with the seventeenth aspect including the step of mixing the first part of the additive solution with the second part of the additive solution in a container separate from and in flow communication with the container of the biological fluid component.

A twenty-second aspect of the present subject matter includes the method in accordance with the twenty-first aspect wherein the second container includes a narrowing flow path to provide a Venturi effect.

A twenty-third aspect of the present subject matter includes the method of any one of the fourteenth through twenty-second aspects including automatically opening a flow path between the container of the biological fluid component and at least a container of at least one of the first and second parts of the additive solution under the direction of the controller.

A twenty-fourth aspect of the present subject matter includes the method in accordance with any one of the fourteenth through twenty-third aspects including automatically opening flow paths between the container of the biological fluid component and (a) the container of the first part of the additive solution and (b) a container of the second part of the additive solution at the direction of the controller.

A twenty-fifth aspect of the present subject matter includes the method in accordance with any one of the fourteenth through twenty-fourth aspects including the step of the container containing the first part of an additive solution onto the reusable hardware unit, mounting a container of the second part of the additive solution onto the reusable hardware unit, associating and aligning a flow blocker and a flow path between one of the containers and a container of the biological fluid component with a flow path opening device of the reusable hardware unit.

While described in terms of the illustrated embodiments, it will be understood that the features and the implementations of the illustrated embodiments may be varied in a manner apparent to those skilled in the art.

The invention claimed is:

1. A method for processing red blood cells and combining said red blood cells with at least one part of a two-part red blood cell additive solution, said method comprising:
   a) mounting onto a reusable hardware unit, selected pre-attached containers of a disposable fluid processing circuit, said fluid circuit comprising (i) a container of blood that has been separated into two or more components wherein one of said separated components comprises red blood cells, (ii) a subassembly of containers of at least three containers wherein a first of said containers contains a first part of an additive solution selected for the prolonged storage of red blood cells, a second of said containers contains a second part of said additive solution downstream of said first of said containers, a third container downstream of said second of said containers for receiving said red blood cells from said container of blood that has been separated into two or more components, a leukoreduction filter downstream of said container for receiving said red blood cells and a filtrate container downstream of said leukoreduction filter, (iii) openable flow paths joining said at least first, second and third containers, and (iv) a flow blocker in an openable flow path,
   said reusable hardware unit including (i) two container holders wherein said first and second containers of said subassembly are each separately received within said two container holders and wherein said two container holders include press plates, (ii) a flow path opening device associated with each of said two container holders and (iii) a controller configured to actuate said flow path opening device and activate said press plates of said container holders at a selected time;
   b) placing said container of blood that has been separated into blood components in a container holder of said reusable hardware unit;
   c) activating the press plates of said holder in which said container of blood is placed and expressing at least said red blood cells to said container for receiving said red blood cells;
   d) placing said first and second containers of said subassembly in said two container holders, respectively and automatically opening a flow path between said third container and at least said second container of said subassembly; and
   e) activating said press plate holding said second container to express therefrom a selected amount of the contents of the second container to the third container to obtain a combined suspension of said red blood cells and said selected amount of the contents of said second container.

2. The method of claim 1 further comprising passing the combined suspension of said red blood cells and said selected amount of the contents of said second container through said leukoreduction filter to collect in the filtrate container.

3. The method of claim 2 comprising, after collecting the combined suspension in the filtrate container, automatically opening a flow path between said first container and said second container of said subassembly.

4. The method of claim 3 further comprising, after automatically opening the flow path between said first container and said second container, flowing the first part of the additive solution through the second container, the third container, and then through the leukoreduction filter to rinse said leukoreduction filter with said first part of said additive solution.

5. The method of claim 4 further comprising collecting the first part of the additive solution in the filtrate container after passing it through the leukoreduction filter, thereby combining the first part of the additive solution with the combined suspension of said red blood cells and said selected amount of the contents of said second container.

6. The method of claim 1 comprising automatically opening flow paths between the container for receiving said red blood cells and (a) the first container containing said first part of the additive solution and (b) the second container containing said second part of the additive solution under the direction of the controller.

7. The method of claim 1 comprising mounting said first container containing a first part of an additive solution onto said reusable hardware unit, mounting said second container containing said second part of said additive solution onto said reusable hardware unit, and associating and aligning a flow blocker in a flow path between one of said first and second containers and said third container with a flow path opening device of said reusable hardware unit.

8. The method of claim 1 wherein said first and second containers of said subassembly are made of flexible material and are compressible.

9. The method of claim 1 further comprising activating said press plates of said two container holders sequentially.

10. The method of claim 1 comprising removing said container of blood that has been separated into two or more components from said reusable hardware unit prior to mounting said containers of said subassembly onto said reusable hardware unit.

11. The method of claim 10 comprising placing one of said first and second containers of said subassembly into said holder from which said container of blood that has been separated into two or more components has been removed and activating said press plate.

\* \* \* \* \*